United States Patent [19]
Hankovsky et al.

[11] 3,941,788
[45] Mar. 2, 1976

[54] BENZIMIDAZOLE DERIVATIVES

[75] Inventors: Olga Hankovszky; Kalman Hideg, both of Hajnoczy; Sandor Pacsa, Pollack, all of Hungary

[73] Assignee: Richter Gedeon Vegyeszeti Gyar Rt, Budapest, Hungary

[22] Filed: Apr. 24, 1974

[21] Appl. No.: 463,686

[30] Foreign Application Priority Data
May 9, 1973 Hungary.................................. RI-508

[52] U.S. Cl.......... 260/256.4 F; 260/309.2; 424/251
[51] Int. Cl.[2]....................................... C07D 239/06
[58] Field of Search.............................. 260/256.4 F

[56] References Cited
UNITED STATES PATENTS
3,468,888   9/1969   Chow .......................... 260/256.4 F Primary Examiner—Richard J. Gallagher
Assistant Examiner—James H. Turnipseed
Attorney, Agent, or Firm—Toren, McGeady and Stanger

[57] ABSTRACT

New benzimidazole derivatives of the general formula (I)

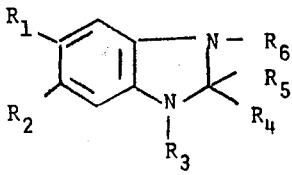

and acid addition salts thereof, wherein
$R_1$ and $R_2$ each represent hydrogen or methyl,
$R_5$ and $R_6$ form together a valence bond and at the same time $R_3$ and $R_4$ form together a group of the general formula (II),

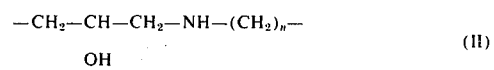

wherein $n$ is equal to zero or one, or
$R_4$, $R_5$ and $R_6$ form together a group of the formula (III)

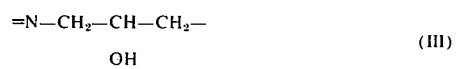

and at the same time $R_3$ stands for benzyl group, were prepared by reacting a compound of the general formula (IV),

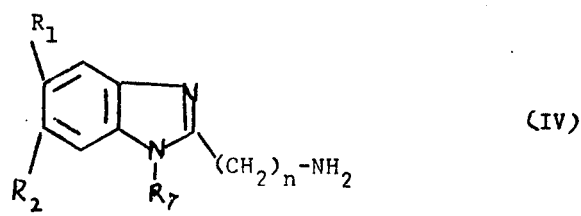

wherein $R_7$ stands for hydrogen or benzyl group and $R_1$, $R_2$ and $n$ each have the same meanings as defined above, or an acid addition salt thereof with epichlorohydrine optionally in the presence of a base.

The new compounds of the general formula (I) and their acid addition salts inhibit the reproduction of viruses and can be used in therapy as antiviral agents.

3 Claims, No Drawings

BENZIMIDAZOLE DERIVATIVES

This invention relates to new benzimidazole derivatives having the general formula (I)

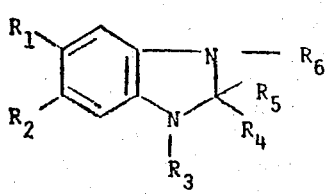

and acid addition salts thereof, wherein $R_1$ and $R_2$ each represent hydrogen or methyl, $R_5$ and $R_6$ form together a valence bond and at the same time $R_3$ and $R_4$ form together a group of the general formula (II),

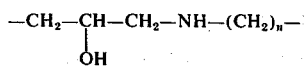

wherein $n$ is equal to zero or one, or $R_4$, $R_5$ and $R_6$ form together a group of the formula (III)

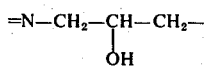

and at the same time $R_3$ stands for a benzyl group.

The invention relates further to a process for the preparation of the above compounds.

We have found that the compounds of the general formula (I) exert an inhibiting effect on the reproduction of viruses.

Several references have been published on the inhibiting effect exerted by certain compounds of benzimidazole skeleton on the reproduction of viruses. In the early stage of the investigations Thompson reported on the inhibiting effect of benzimidazole exerted on the reproduction of vaccinia virus, the activity of this compound, however, proved to be poor even at very high concentrations (Thompson, R. L.: J Immunol. 55, 345 /1947/; ref.: C.A. 41, 4829 /1947/).

Starting from the structure of vitamine $B_{12}$, the inhibiting effect exerted by 5,6-dimethyl-1-α-D-ribofuranosyl-benzimidazole and 5,6-dichloro-1-α-D-ribofuranosyl-benzimidazole on influenza viruses was investigated later on (Bauer, D. J.: Brit. J. Exptl. Pathol. 36, 105 /1955/; Tamm, I., Folkers, K., Horsfall, F. L. Jr.: Yale J. Biol. Med., 24, 559 /1952/). These compounds, however, did not prove to be as effective under in vivo conditions as expected (Kissmann, H. M., Child, R. G., Weiss, M. J.: J. Am. Chem. Soc. 79, 1185 /1957/).

The most thoroughly examined compound of the benzimidazole derivatives is 2-(α-hydroxybenzyl)-benzimidazole (HBB). Its inhibiting effect on the reproduction of polio viruses was described in 1958 (Hollingshead A. C., Smith, P. K.: J. Pharmacol. Exptl. Therap., 123, 54 /1958/), and its effect on other viruses has also been examined in detail (Eggers H. J., Tamm, I.: Virology, 18, 426 /1962/).

Certain other benzazole derivatives, i.e., benzthiazoles and benzoxazoles, have a medium inhibiting effect on the reproduction of influenza virus under in vitro conditions (Váczi L., Hadházy, Gy., Hideg, K., Gergely, L., Hankovszky, O., Toth, F. D.: Acta Virol. 12, 371 /1968/). According to the investigations of Eggers et al. (Eggers, H. J., Tamm, I.: Annual Review of Pharmacology, Vol. 6., 231 /1966/), the benzimidazole compounds exert a perceptible action only on the small RNS viruses belonging to the picorna group.

Among the substituted benzimidazole derivatives of the invention containing an N-heterocyclic group a significant inhibiting effect on the reproduction of viruses was observed for the following compounds:

1,2,3,4-tetrahydro-3-hydroxy-pyrimido[1,2-a]benzimidazole, 3,4-dihydro-3-hydroxy-7,8-dimethyl-10-benzyl-2H-pyrimido-[1,2-a]-benzimidazoline, and 2,3,4,5-tetrahydro-4-hydroxy-1H-(1,4)-diazepino[1,2-a]benzimidazole.

An outstanding representative of this group is 1,2,3,4-tetrahydro-3-hydroxy-pyrimido[1,2-a]benzimidazole, which also inhibits the reproduction of DNS-containing viruses.

The inhibiting effect of the compounds exerted on the reproduction of viruses were examined by the method of Millar et al. (J. D. Millar, R. R. Roberto, H. Wulff, H. A. Wenner, D. A. Henderson: Bull. Wld. Hlth. Org. 41, 749–760 /1969/). According to this method tissue cultures filled into test tubes were infected with different amounts of vaccinia virus (the amount of the virus being expressed in plaque forming units, (PFU), and the number of plaques developed in the cultures containing the compound to be tested was compared to that in the control cultures. It is to be noted that the plaques evoked by the virus can be counted easily in tube cultures, without using an agar layer.

The extent of inhibition was expressed as the percentage decreased of the plaque number with respect to the controls. On the basis of this test we have found that, e.g., 2,3,4,5-tetrahydro-3-hydroxypyrimido[1,2-a]benzimidazole in an amount of 80 μg./ml. exerts a 100 % inhibiting effect on 100 to 300 PFU of vaccinia virus, and even for extremely high virus dosages ($5 \times 10^4$PFU) an inhibiting effect over 95% can be achieved by the same active agent concentration.

The above compound also exerts an inhibiting effect in lower concentrations against lower amounts of viruses, thus, e.g., in an amount of 5 μg./ml. the compound has a 40% inhibiting effect on the reproduction of the virus in a dosage of 200 PFU, whereas in an aount of 10 μg./ml. the compound exerts a complete inhibition on the same virus dosage.

In these experiments the strain of Lancy viruses adapted to HEp-2 tissue culture was used.

The new compounds of the general formula (I), wherein $R_1$, $R_2$, $R_3$, $R_4$, $R_5$ and $R_6$ each have the same meanings as defined above, as well as the acid addition salts thereof can be prepared according to the invention by reacting a compound of the general formula (IV)

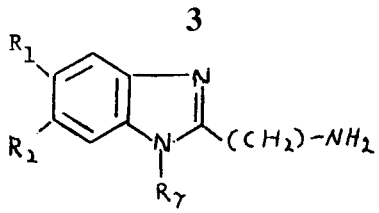

(IV)

wherein $R_7$ stands for hydrogen or benzyl group and $R_1$, $R_2$ and $n$ each have the same meanings as defined above, or an acid addition salt thereof, with epichlorohydrine optionally in the presence of a base, preferably alkali metal hydroxide, and, if desired, converting the thus-obtained free bases into their salts, or alternately, converting the thus-obtained salts into the free bases.

The benzimidazole derivatives of the general formula (IV), used as starting substance in the process of the invention, are known compounds.

The process of the invention is carried out preferably by dissolving or suspending a compound of the general formula (IV) in an inert solvent, such as alkanol or acetone, and thereafter adding the appropriate amount of epichlorohydrine and an organic or mineral base, such as an alkali hydroxide serving to bind the hydrochloric acid formed in the reaction, to the mixture. Epichlorohydrine may be used in stoichiometric amount or in a slight excess.

The acid binding agent can be added separately or together with the epichlorohydrine, one may also proceed, however, by adding first the acid binding agent and thereafter the epichlorohydrine to the reaction mixture. The organic or mineral base can be administered in the solid state or in the form of a solution or suspension formed with water or an aqueous organic solvent.

The reaction of the compound having the general formula (IV) with epichlorohydrine in the presence of an acid binding agent is in general carried out at elevated temperatures, preferably at the boiling point of the reaction mixture. The progress of the reaction can be monitored by the separation of the inorganic halide; i.e., the reaction is completed when the halide ceases to separate.

According to an advantageous method of the invention the separation of the halide salt in the form of an insoluble precipitate is ensured by properly selecting the amount and the nature of the solvent, whereby the end-product can be separated easily from the by-product.

As acid-binding agent, preferably an alkali or alkaline earth metal hydroxide, such as sodium hydroxide, potassium hydroxide, hydrated lime oxide, etc., is used.

In general, the compounds of the general formula (IV) are purchased in the form of their acid addition salts, as the salts of these compounds have an increased stability. The process of the invention is applicable to the acid addition salts of the compounds of the general formula (IV) as well. In this event a base, stronger than the benzimidazole base in question and thus capable of liberating the latter from its salt, is used in the reaction. The free bases are liberated according to known procedures. According to a preferred method alkali metal or alkaline earth metal hydroxides are added to the mixture in an amount also sufficient to bind the hydrochloric acid formed in the subsequent reaction with epichlorohydrine. The other steps of the reaction are the same as described above.

The compounds of the general formula (I) are generally separated after the removal of the solvent in the form of the free bases. These bases can be converted into their acid addition salts using calculated amounts of an organic or mineral acid.

The compounds of the invention can be converted into pharmaceutical products using organic or mineral carriers inert towards the active agents and suitable for enteral or parenteral administration.

The pharmaceutical compositions may contain the new compounds of the general formula (I) either alone or in combination with other known active agents.

If desired, the pharmaceutical products can be sterilized, or admixed with other auxiliary substances, such as salts influencing the osmotic pressure, buffers, etc.

The invention is elucidated in detail by the aid of the following non-limiting Examples.

EXAMPLE 1

1,2,3,4-Tetrahydro-3-hydroxy-pyrimido[1,2-a]benzimidazole hydrochloride 1.33 g. (0.01 moles) of 2-amino-benzimidazole are dissolved in 100 ml. of alcohol, and 0.4 g. (0.01 moles) of sodium hydroxide dissolved in 5 ml. of water are added to the mixture, followed by the addition of 0.92 g. (0.01 moles) of epichlorohydrine. The reaction mixture is boiled for about 3 hours. The reaction is completed when the inorganic salt ceases to separate. The separated sodium chloride is filtered off, washed with 2 × 5 ml. of alcohol, and the combined filtrate and wash is evaporated to dryness. 1.8 g. (80%) of white, crystalline 1,2,3,4-tetrahydro-3-hydroxy-pyrimido[1,2-a]benzimidazole are obtained; m.p.: 158°–160°C (heating rate: 4°C/min.).

Analysis: Calculated for $C_{10}H_{11}N_3O$ (189.21): C: 63.48%, H: 5.86%, N: 22.21%. Found: C: 63.24%, H: 5.80%, N: 22.34%.

The base is dissolved in a mixture of acetone and alcohol, and the solution is acidified to pH 3 with hydrochloric acid. The separated white crystals are filtered off and recrystallized from a 1:1 mixture of alcohol and ether. 1,2,3,4-Tetrahydro-3-hydroxy-pyrimido[1,2-a]benzimidazole hydrochloride is obtained with a yield of 89%. M.p.: 214°–216°C (heating rate: 4°C/min.).

Analysis: Calculated for $C_{10}H_{11}N_3O \cdot HCl$ (225.68): C: 53.22%, H: 5.36%, N: 18.62%, Cl: 15.71%. Found: C: 53.47%, H: 5.57%, N: 18.18%, Cl: 16.09%.

NMR-spectrum (in $D_2O$): 6.6 to 5.6 (complex, 5H, aliphatic protons); 2.63 (4H, *m*, aromatic protons).

EXAMPLE 2

3,4-Dihydro-3-hydroxy-7,8-dimethyl-10-benzyl-2H-pyrimido[1,2-a]benzimidazoline hydrochloride 2.51 g. (0.01 moles) of 1-benzyl-2-amino-5,6-dimethyl-benzimidazole are suspended in 100 ml. of alcohol, 5 ml. of an aqueous sodium hydroxide solution are added, and the solids are dissolved in the reaction medium under gentle heating. Thereafter 0.92 g. (0.01 moles) of epichlorohydrine are added, and the mixture is boiled until the separation of sodium chloride ceases. The reaction mixture is cooled, the sodium chloride is removed by filtration, and washed with alcohol. The combined filtrate and wash is evaporated to dryness. The solid residue is dissolved in a mixture of ether and alcohol, and the solution is acidified to pH 3 with hydrochloric acid. The separated white crystals are filtered off, washed with a small amount of the solvent, and dried.

2.8 g. (82%) of 3,4-dihydro-3-hydroxy-7,8-dimethyl-10-benzyl-2H-pyrimido[1,2-a]benzimidazoline hydrochloride are obtained; m.p.: 243°–245°C (heating rate: 4°C/min.).

After recrystallization from a mixture of alcohol and ether, the product melts at 258°–260°C (heating rate: 4°C/min.).

Analysis: Calculated for $C_{19}H_{21}N_3O.HCl$ (343.86): C: 66.37%, H: 6.45%, N: 12.22%, Cl: 10.31%. Found: C: 66.10%, H: 6.22%, N: 12.22%, Cl: 9.99%.

EXAMPLE 3

2,3,4,5-Tetrahydro-4-hydroxy-1H-(1,4)-diazepino-[1,2-a]benzimidazole dihydrochloride 22 g. (0.1 moles) of 2-aminomethyl-benzimidazole dihydrochloride are suspended in 250 ml. of alcohol, and an alcohol solution of 12 g. (0.3 moles) of sodium hydroxide is added slowly to the cooled suspnesion. Thereafter 9.2 g. (0.1 moles) of epichlorohydrine are added to the mixture, and the reaction mixture is boiled for 3 hours under reflux. The mixture is cooled, the sodium chloride is removed by filtration, and the filtrate is evaporated to dryness under reduced pressure. The oily residue is dissolved in a mixture of acetone and alcohol, and the pH of the solution is adjusted to 3 with hydrochloric acid. The separated white, crystalline substance is filtered off, washed with a small amount of the above solvent, and dried. This way 20.9 g. (76%) of 2,3,4,5-tetrahydro-4-hydroxy-1H-(1,4)-diazepino[1,2-a]benzimidazole dihydrochloride are obtained; m.p.: 248°–250°C (heating rate: 4°C/min.).

After recrystallization from a mixture of alcohol and ether, the product melts at 251°–253°C (heating rate: 4°C/min.).

Analysis: Calculated for $C_{11}H_{13}N_3O$ .2HCl (276.16): C: 47.84%, H: 5.47%, N: 15.22%, Cl: 25.68%. Found: C: 47.26%, H: 5.26%, N: 14.91%, Cl: 24.99%.

NMR-spectrum (in $D_2O$): 6.13 (2H, $d$), 4.90 to 5.40 (3H, $m$, complex), 4.88 (2H, $s$), 2.17 (4H, $m$, aromatic protons).

What we claim is:
1. a compound of the formula (I)

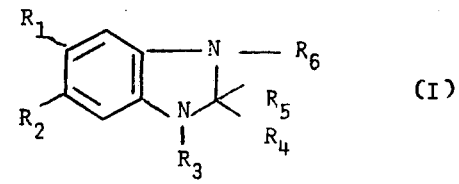

or a hydrochloride addition salt thereof, wherein
$R_1$ and $R_2$ each represent hydrogen or methyl,
$R_5$ and $R_6$ form together a valence bond and at the same time $R_3$ and $R_4$ form together a group of the formula (II),

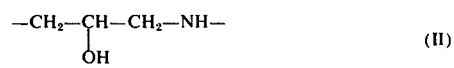

or
$R_4$ and $R_5$ and $R_6$ form together a group of the formula (III)

and at the same time $R_3$ stands for benzyl group.
2. 1,2,3,4-Tetrahydro-3-hydroxy-pyrimido[1,2-a]benzimidazole or the hydrochloride addition salt thereof.
3. 3,4-Dihydro-3-hydroxy-7,8-dimethyl-10-benzyl-2H-pyrimido[1,2-a]benzimidazoline or the hydrochloride addition salt thereof.

* * * * *